(12) United States Patent
Shin et al.

(10) Patent No.: US 7,378,006 B2
(45) Date of Patent: May 27, 2008

(54) AQUEOUS SOLUTIONS FOR REDUCING THE RATE OF OXYGEN LOSS, AND METHODS THEREOF

(75) Inventors: Jungwon Shin, Andover, MA (US);
Sohrab Mansouri, Sudbury, MA (US);
Dennis Conlon, Shirley, MA (US)

(73) Assignee: Instrumentation Laboratory Company, Lexington, MA (US)

( * ) Notice: Subject to any disclaimer, the term of this patent is extended or adjusted under 35 U.S.C. 154(b) by 702 days.

(21) Appl. No.: 10/625,984

(22) Filed: Jul. 24, 2003

(65) Prior Publication Data

US 2004/0137633 A1 Jul. 15, 2004

Related U.S. Application Data

(60) Provisional application No. 60/398,661, filed on Jul. 26, 2002.

(51) Int. Cl.
*G01N 27/327* (2006.01)
*G01N 31/00* (2006.01)

(52) U.S. Cl. ............... 204/400; 204/403.1; 436/8; 205/792

(58) Field of Classification Search ............ 204/403.01–403.15; 205/777.5, 778, 792; 436/8, 436/9, 11
See application file for complete search history.

(56) References Cited

U.S. PATENT DOCUMENTS

| | | | | |
|---|---|---|---|---|
| 4,245,050 A | * | 1/1981 | Nakanishi et al. | ......... 435/191 |
| 4,686,002 A | * | 8/1987 | Tasset | ............... 216/100 |
| 4,734,184 A | | 3/1988 | Hurley et al. | ......... 204/409 |
| 5,209,858 A | * | 5/1993 | Heinsohn et al. | ......... 252/1 |
| 5,256,571 A | | 10/1993 | Hurley et al. | ............ 436/17 |
| 5,705,482 A | | 1/1998 | Christensen et al. | ...... 514/12 |
| 6,143,545 A | | 11/2000 | Clausen et al. | .......... 435/198 |
| 6,200,947 B1 | | 3/2001 | Takashima et al. | ...... 510/402 |
| 6,482,416 B2 | | 11/2002 | Munn et al. | ........... 424/278.1 |
| 6,652,720 B1 | | 11/2003 | Mansouri et al. | ..... 204/403.11 |
| 6,960,466 B2 | | 11/2005 | Pamidi et al. | ......... 435/287.1 |
| 2003/0000833 A1 | | 1/2003 | Mansouri et al. | ......... 204/402 |
| 2003/0062262 A1 | | 4/2003 | Mansouri et al. | ......... 204/400 |

FOREIGN PATENT DOCUMENTS

| | | |
|---|---|---|
| RU | 649396 | 2/1979 |
| WO | EP 03/62032 | 4/1990 |
| WO | WO 93/21533 | 10/1993 |
| WO | EP 08/72726 | 10/1998 |

OTHER PUBLICATIONS

"Water on the Web: The Chemistry of Oxygen Solubility Reading" downloaded www.wateronteh web.org/curricula/bs/student/oxygen/reading.html on Jun. 21, 2007.*

(Continued)

*Primary Examiner*—Alex Noguerola
(74) *Attorney, Agent, or Firm*—Kirkpatrick & Lockhart Preston Gates Ellis LLP (57) ABSTRACT

Compositions and methods for reducing the rate of loss of oxygen from a solution and increasing the effective life span of oxygen-containing calibration solutions.

52 Claims, 2 Drawing Sheets

OTHER PUBLICATIONS

Doretti et al. ("Covalently immobilized enzymes on biocompatible polymers for amperometric sensor applications," Biosensors and Bioelectronics vol. 11, No. 4, pp. 365-373, 1996).*

Baraona et al.: Effects of Alcohol and Polyenylphosphatidylcholine on Hepatic Nitric Oxide Production and its Peroxynitrite-Mediated Toxicity, *Alcoholism Clinical and Experimental Research*, vol. 24, No. 5 Supplement, pp. 200A (2000) (Abstract only).

Bentley et al.: Activation of Superoxide Production and Differential Exocytosis in Polymorphonuclear Leukocytes by Cytochalasins A, B, C, D and E : Effects of Various Ions, *Biochimica et Biophysica Acta*, vol. 678, pp. 238-244 (1981).

Cho et al.: Effects of Choline Chloride and its Analogues on Photosynthesis in Wheat Protoplasts, *Proceedings of the Fourteenth Annual Plant Growth Regulator Society of America Meeting*, pp. 131-134 (1987).

Huntsman et al.: Nucleus-Specific Differences in $GABA_A$ - Receptor-Mediated Inhibition Are Enhanced During Thalamic Development, The American Physiological Society 2000.

Jürgens et al.: Delay copper-catalyzed oxidation of low density lipoprotein by in vitro enrichment with choline or ethanolamine plasmalogens, *Chemistry and Physics of Lipids*, vol. 77, No. 1, pp. 25-31 (1995).

Lippman: The Prolongation of Life: A Comparison of Antioxidants and Geroprotectors Versus Superoxide in Human Mitochondria, *Journal of Gerontology*, vol. 36, No. 5, pp. 550-557 (1981).

Meyer et al.: Effects of Peroxidation and Aging on Rat Neocortical ACh-Release and Protein Kinase C, *Neurobiology of Aging*, vol. 15, No. 1, pp. 63-67 (1994).

Saito et al.: Antioxidant Activity and Active Sites of Phospholipids and Antioxidants, *Journal of the American Oil Chemists' Society*, vol. 74, No. 12, pp. 1531-1536 (1997).

Williams et al.: Cerebral Microvessel Phospholipase $A_2$ Activity in Senescent Mouse, *Neurochemical Research*, vol. 19, No. 3, pp. 317-320 (1994).

Wilson et al.: Vascular Damage and Lipid Peroxidation in Choline-deficient Rats, *Experimental and Molecular Pathology*, vol. 18, No. 3, Jun. 1973.

Wu et al.: Alzheimer's Amyloid-Beta Peptide Inhibits Sodium/ Calcium Exchange Measured in Rat and Human Brain Plasma Membrane Vesicles, *Neuroscience*, vol. 80, No. 3, pp. 675-684 (1997).

Kruk: The use of biologically active substances in the freezing of boar semen, *Zootekhniya*, vol. 10, pp. 28-30 (1996) (English abstract attached.).

Storozhok et al.: Synergic Effects in the Combined Antioxidant Action of Phosphatidyl Choline with Native and Artificial Quinones, *Vopr. Med. Khim*, vol. 40, Issue 1 pp. 10-14 (1994).

International Search Report for PCT/US03/23138 mailed Nov. 25, 2003

Enami: Effects of Pheny N-*tert*-Butyl Nitrone and its Derivatives on Hepatocarcinogenesis in Rats Fed a Choline-Deficient, L-Amino Acid-Defined Diet, *Journal of Nara Medical Association*, vol. 51, No. 6, pp. 468-482 (2000).

Erecinska: Stimulation of the NA+/K+ Pump Activity During Electrogenic Uptake of Acidic Amino Acid Transmitters by Rat Brain Synaptosomes, *Journal of Neurochemistry*, vol. 52, pp. 135-139 (1989).

Farombi et al.: Antioxidant activity of palm oil carotenes in peroxyl radical-mediated peroxidation of phosphatidyl cholines liposomes, *Redox Report*, vol. 4, No. 1/2, pp. 61-68 (1999).

Farombi et al.: Antioxidant activity of palm oil carotenes in organic solution: effects of structure and chemical reactivity, *Food Chemistry*, vol. 64, No. 3, pp. 315-321 (1999).

Farombi et al.; Evalutation of the Antioxidant activity and partial characterisation of extracts from browned yam flour diet, *Food Research International*, vol. 33, No. 6, pp. 493-499 (2000).

Fiedler et al.: Die Wirkung von Cholinchlorid auf den O2-Gehalt des arteriellen Blutes bei Lebererkrankungen, *Dtsch. Ceitschr. F. Verdauungs- i. Stoffwechselkrankheiten*, vol. 26, pp. 79-84 (1966).

Kaul et al.: Plant Polyphenols Inhibit Benzoyl Peroxide-induced Superoxide Anion Radical Production and Diacylglyceride Formation in Murine Peritoneal Macrophage, *Nutrition and Cancer*, vol. 35, No. 2, pp. 207-211 (1999).

Nakae et al.: Preventive Effects of Various Antioxidants on Endogenous Liver Carcinogenesis in Rats Fed a Choine-Deficient, L-Amino Acid-Defined Diet, *Food Factors for Cancer Prevention*, pp. 92-97.

Phung et al.: Role of Antioxidants in Inhibiting Hepatic Fibrosis in a Murine Nutritional Model of Nash, *Hepatology*, vol. 32, No. 4 (Abstract only).

West et al.: Proton translocation by cytochrome oxidase in (antimycin + myxothiazol)-treated rat liver mitochondria using ferrocyanide or hexammineruthenium as electron donor, *Biochemistry Journal*, vol. 236, No. 1, pp. 15-21 (1986).

Wilson et al.: Protection by Antioxidants Against Arterial Sclerosis of Chronic Choline-Deficiency, *Experimental and Molecular Pathology*, vol. 21, pp. 118-122 (1974).

Wydrzynski et al.: Selective Inhibition of Photosystem II Reactions from Water Splitting to Q Reduction is Thylakoid Samples by Lauroyl Choline Chloride: Evidence from Fluorescence Transient Measurements, *Advances to Photosynthests Research*, vol. 1, pp. 437-440 (1984).

Dehlawi et al.: Choline Derivatives and Sodium Fluoride Protect Acetylcholinesterase against Irreversible Inhibition and Aging by DFP and Paraoxon, *Journal of Biochemical Toxicology*, vol. 9, No. 5, pp. 261-268 (1994).

Ghoshal et al.: Prevention by Free Radical Scavenger $AD_3$ of Prooxidant Effects of Choline Deficiency, *Free Radical Biology & Medicine*, vol. 8, pp. 3-7 (1990).

Grattagliano et al.: Starvation Impairs Antioxidant Defense in Fatty Livers of Rats Fed A Choline-Deficient $Diet_1$, *The Journal of Nutrition*, vol. 130, No. 9, pp. 2131-2136.

Hiramatsu et al.: Free radicals, lipid peroxidation, SOD activity, neurotransmitters and choline acetyltransferase activity in the aged rat brain, *Free Radicals and Aging*, pp. 213-218, 1992.

* cited by examiner

AQUEOUS SOLUTIONS FOR REDUCING THE RATE OF OXYGEN LOSS, AND METHODS THEREOF

RELATED APPLICATIONS

This application claims the benefit of U.S. Provisional Application Ser. No. 60/398,661, filed on Jul. 26, 2002, the entire disclosure of which is hereby incorporated by reference.

FIELD OF THE INVENTION

The present invention is related to the field of electrochemical sensors, and calibration solutions, particularly to the increased accuracy and effective life span of oxygen sensors.

BACKGROUND OF THE INVENTION

In a variety of clinical situations it is important to measure certain chemical characteristics of the patient's blood such as pH, hematocrit, the concentration of calcium ions, potassium ions, chloride ions, sodium ions, glucose, lactate, creatinine, urea, the partial pressure of oxygen ($O_2$), carbon dioxide ($CO_2$), and the like. These situations range from a routine visit of a patient in a physician's office to monitoring of a patient during open-heart surgery. The required speed, accuracy, and other performance characteristics vary with each situation.

Typically, electrochemical sensor systems which provide blood chemistry analysis are stand-alone machines or are adapted to be connected to an extracorporeal shunt or an ex vivo blood source such as a heart/lung machine used to sustain a patient during surgery. Thus, for example, small test samples of ex vivo blood can be diverted off-line from either the venous or arterial flow lines of a heart/lung machine directly to a chamber exposed to a bank of microelectrodes which generate electrical signals proportional to chemical characteristics of the real time flowing blood sample.

Electrochemical sensor systems are analytical tools combining a chemical or biochemical recognition component (e.g., an enzyme) with a physical transducer such as a platinum electrode. The chemical or biochemical recognition component is capable of selectively interacting with an analyte of interest and of generating, directly or indirectly, an electrical signal through the transducer. Electrochemical sensor systems play an increasing role in solving analytical and clinical problems, and find applications in the field of medical diagnostics.

The selectivity of certain biochemical recognition components makes it possible to develop electrochemical sensors that can accurately detect certain biological analytes even in a complex analyte mixture such as whole blood. Despite the high degree of selectivity of electrochemical sensors, the accuracy of such sensors depends on calibrating the sensor against a calibration solution that includes a known concentration of analyte. If the actual concentration of the analyte in the calibration solution is different from the concentration assumed to be in the solution, then the sensor may be improperly calibrated and the sensor readings may be inaccurate. The oxygen in a calibration solution may be removed by, for example, the oxidation of other components of the solution or contaminants in the solution. The amount of oxidation that occurs in the calibration solution is unpredictable and, over a period of time, may lead to an oxygen content in the calibration solution different from the oxygen content estimated to exist from the preparation of the solution. A calibration solution in which the oxygen content is unknown and may be different from the estimated value may lead to an incorrect calibration of the sensor and inaccurate sensor readings.

SUMMARY OF THE INVENTION

One objective of the present invention is to provide a system and a method for increasing the accuracy and effective life span of an electrochemical sensor system, in particular a calibrating solution required for the calibration of an oxygen sensor of the electrochemical sensor system. According to the invention described herein, the addition of choline to an oxygen-containing solution such as a calibrating solution, for example, reduces the rate at which oxygen is lost from the solution. The reduction in the rate of loss of oxygen content of the solution stabilizes the oxygen content in the solution over a period of time. The stabilized oxygen content in a calibration solution increases the effective life span of the calibration solution's ability to accurately calibrate an oxygen sensor.

In one aspect of the present invention, a solution for the calibration of an oxygen sensor includes a selected concentration of choline and a known oxygen content. The concentration of choline is sufficient to reduce a rate of loss of oxygen content in the solution, and the known oxygen content is at a level sufficient to calibrate an oxygen sensor. In one embodiment, the rate of loss of oxygen in the solution is in the range of about 0.05 millimeters of mercury/month (mmHg/month) to about 5.0 mmHg/month. In one embodiment, the choline in the solution includes choline chloride. In alternative embodiments, other choline salts such as choline hydrogen citrate, choline bitartrate, choline bicarbonate, tricholine citrate, choline ascorbate, choline borate, choline gluconate, choline phosphate, choline di(choline) sulphate and dicholine mucate may be sources of choline in the solution. In one embodiment, the choline concentration in the solution is in the range of about 5 millimoles/liter (mmol/L) to about 100 mmol/L. In another embodiment, the choline concentration in the solution is about 20 mmol/L.

In one embodiment of the invention, the oxygen content in the solution is in the range of about 10 mmHg to about 300 mmHg. In other embodiments of the invention, the oxygen content in the solution is about 100 mmHg or about 180 mmHg.

In one embodiment of the present invention, the solution for the calibration of an oxygen sensor further includes $CO_2$. The solution may also include helium gas. In another embodiment the solution may include $Na^+$, $K^+$, $Ca^{++}$, and/or $HCO_3^-$. Such compounds may function as calibration standards for electrochemical sensors specific to the compound. In another embodiment, the solution further includes a surfactant. The solution may also include an inert preservative and/or a biological buffer.

In one aspect of the present invention, a container of calibration solution for calibrating an electrochemical sensor includes a selected concentration of choline and a known concentration of oxygen. The container for holding the calibration solution is substantially gas-impermeable. According to this aspect of the invention, the concentration of choline is sufficient to reduce a rate of loss of oxygen content in the solution, and the oxygen content in the solution is at a level sufficient to calibrate an oxygen sensor. In one embodiment, the container includes at least one flexible wall that allows for contraction of a volume of the container. The flexible wall allows the volume of the container to decrease as the solution is drawn out of the container. In another embodiment, the container enclosing the calibration solution is sealed to prevent a headspace that includes a gas.

In one embodiment of the container, the choline in the solution includes choline chloride. In alternative embodiments of the container, other choline salts such as choline hydrogen citrate, choline bitartrate, choline bicarbonate, tricholine citrate, choline ascorbate, choline borate, choline gluconate, choline phosphate, choline di(choline)sulphate and dicholine mucate, may be included in the solution. In one embodiment of the container, the choline concentration in the solution is in the range of about 5 mmol/L to 100 mmol/L. In another embodiment, the choline concentration in the solution is about 20 mmol/L.

In another embodiment of the container, the oxygen content in the solution is in the range of about 10 mmHg to 300 mmHg. In other embodiments of the invention, the oxygen content in the solution is about 100 mmHg and about 180 mmHg.

In yet another embodiment of the container, the solution for the calibration of an oxygen sensor further includes $CO_2$. In other embodiments of the container the solution may further include helium gas, $Na^+$, $K^+$, $Ca^{++}$, and/or $HCO_3^-$. Such compounds may function as calibration standards for electrochemical sensors specific to the compound. In another embodiment, the solution further includes a surfactant. The solution may also include an inert preservative and/or a biological buffer.

In another aspect, the invention relates to a method of reducing a rate of loss of oxygen content in a solution. The method includes providing a solution that includes oxygen dissolved in the solution. The method also includes adding choline to the solution, wherein the choline is added in an amount sufficient to reduce the rate of loss of oxygen content in a solution. In one embodiment, 20 mmol/L choline is added to the solution. In another embodiment, choline is added to the solution in the range of about 5 mmol/L to 100 mmol/L. In another embodiment, choline further includes choline chloride. In yet another embodiment, oxygen in the solution is about 100 mmHg or about 180 mmHg. In another embodiment, oxygen in the solution is in the range of about 10 mmHg to about 300 mmHg.

In another embodiment of the method, the solution includes a calibration solution. In other embodiments, choline salts such as choline hydrogen citrate, choline bitartrate, choline bicarbonate, tricholine citrate, choline ascorbate, choline borate, choline gluconate, choline phosphate, choline di(choline)sulphate and dicholine mucate may be included in the solution. In another embodiment, the solution further includes $CO_2$. In another embodiment, the solution further includes helium gas. In other embodiments of the method, the solution may further include $Na^+$, $K^+$, $Ca^{++}$, $HCO_3^-$, a surfactant, an inert preservative, and/or a biological buffer.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWING

The foregoing and other objects, features and advantages of the present invention disclosed herein, as well as the invention itself, will be more fully understood from the following description of preferred embodiments and claims, when read together with the accompanying drawings. The drawings are not necessarily to scale, emphasis instead generally being placed upon illustrating the principles of the invention.

DETAILED DESCRIPTION OF THE INVENTION

The present invention relates to electrodes and electrochemical sensor systems for measuring oxygen levels of aqueous samples including, but not limited to, blood, serum or other body fluids. Specifically, the invention is directed to improving the effective life span of calibration solutions for calibrating an oxygen sensor by stabilizing the oxygen content of the calibration solution over an extended period of time.

Definitions

In order to more clearly and concisely point out and describe the subject matter which applicant regards as the invention, the following definitions are provided for certain terms used in the following description and claims.

As used herein, the term "electrode" refers to a component of an electrochemical device that makes the interface between the external electrical conductor and the internal ionic medium. The internal ionic medium is typically an aqueous solution with dissolved salts. The medium may also include proteins in a stabilizing matrix.

Electrodes are of three types: working or indicator electrodes, reference electrodes, and counter electrodes. A working or indicator electrode measures a specific chemical species, such as an ion. When electrical potentials are measured by a working electrode, the method is termed potentiometry. All ion-selective electrodes operate by potentiometry. When current is measured by a working electrode, the method is termed amperometry. Oxygen measurement is performed by amperometry. Working electrodes may also function by including an enzyme as part of an enzyme layer that is part of a composite layer that is in close contact with the electrode. The enzyme, which is specific to a particular analyte, may produce hydrogen peroxide, a by-product of the catalytic reaction of the enzyme on the analyte. Hydrogen peroxide is detected by the electrode and converted to an electrical signal. A reference electrode serves as an electrical reference point in an electrochemical device against which electrical potentials are measured and controlled. In one embodiment, silver-silver nitrate forms the reference electrodes. Other types of reference electrodes are mercury-mercurous chloride-potassium chloride or silver-silver chloride-potassium chloride. A counter electrode may act as a sink for the current path.

As used herein, the term "sensor" is a device that responds to variations in the concentration of a given chemical species, such as glucose or oxygen, in a sample, such as a body fluid sample. An electrochemical sensor is a sensor that operates based on an electrochemical principle and requires at least two electrodes. For ion-selective measurements, the two electrodes include an ion-selective electrode and a reference electrode. Amperometric enzyme electrodes additionally require a third electrode, a counter electrode. Moreover, enzyme sensors based on two electrodes, a working and reference electrode, are also common.

As used herein, the term "ion selective electrode" generally refers to a silver wire coated with silver chloride in contact with a buffer solution containing a chloride concentration (the inner solution). The buffer solution may be covered with a polymeric ion-selective membrane that is in contact with the test solution. The ion selective membrane typically includes a high molecular weight polyvinyl chloride (PVC), a plasticizer, an ionophore specific to a particular ion, and a borate salt. The surface of the polymeric membrane is in contact with the test sample on one side and the inner buffer solution on the other side of the membrane.

As used herein, the term "calibration" refers to the process by which the response characteristics of a sensor to a specific analyte are determined quantitatively. To calibrate a sensor, the sensor may be exposed to at least two reagent samples, each reagent sample having a different, known concentration of an analyte. The responses, i.e., signals, measured by the sensor, relative to the concentrations of the analyte in the two different reagent samples, serve as reference points for measurements of the analyte in samples having unknown concentrations of the analyte.

As used herein, the term "oxygen content" refers to the amount of oxygen dissolved in a solution. The oxygen content of a solution may be measured in terms of millimeters of mercury (mmHg). The oxygen content of a solution is analogous to the concentration of an analyte in the solution.

As used herein, the term "starting time point" refers to a time point during the life span of an oxygen-containing solution such as, for example, a calibration solution. The starting time point of the solution may, for example, coincide with or immediately follow the solution being placed into a sealed container. The age of the solution is measured from the starting time point of the solution.

As used herein, the term "original oxygen content" refers to the oxygen content of a solution at the starting time point of the solution.

As used herein, the term "rate of loss of oxygen content" refers to a rate that oxygen is lost from a particular solution in a particular container or environment. The rate of loss of oxygen content is experimentally determined by measuring the loss of oxygen content from a solution over a series of time points. Time points may be measured, for example, daily, weekly, or monthly.

As used herein, the term "estimated rate of loss of oxygen content" refers to, for example, a median or average of rates of loss of oxygen concentration from a plurality of batches of a solution. Each batch of the plurality of batches must have identical compositions, identical methods of preparation, and exist in identical containers or environments for the estimated rate of loss of oxygen content calculated from the plurality of batches to be representative of the rate of loss of oxygen content for any one of the batches. Any variation in the compositions, methods of preparation, or containers or environments between the batches may increase the variability of the rates of loss of oxygen content among the batches. An estimated rate of loss of oxygen content calculated from a plurality of non-identical batches may not be representative of any single batch and thus may not accurately represent the rate of loss of oxygen content for any one solution.

As used herein, the term "estimated oxygen content" refers to a value of oxygen content that is calculated by the electrochemical sensor system in order to, for example, estimate the amount of oxygen in the calibration solution. The estimated oxygen content of the calibration solution is calculated by determining the product of the estimated rate of loss of oxygen content for the calibration solution and the time elapsed since the starting time point of the calibration solution. The resulting product is subtracted from the original oxygen content to determine the estimated oxygen content. The estimated oxygen content is the oxygen content value assigned by the electrochemical sensor system to the calibration solution. The estimated oxygen content of the calibration solution is the value used by the electrochemical sensor system in calibrating the oxygen sensor.

Electrochemical Sensor System

Figure 1:
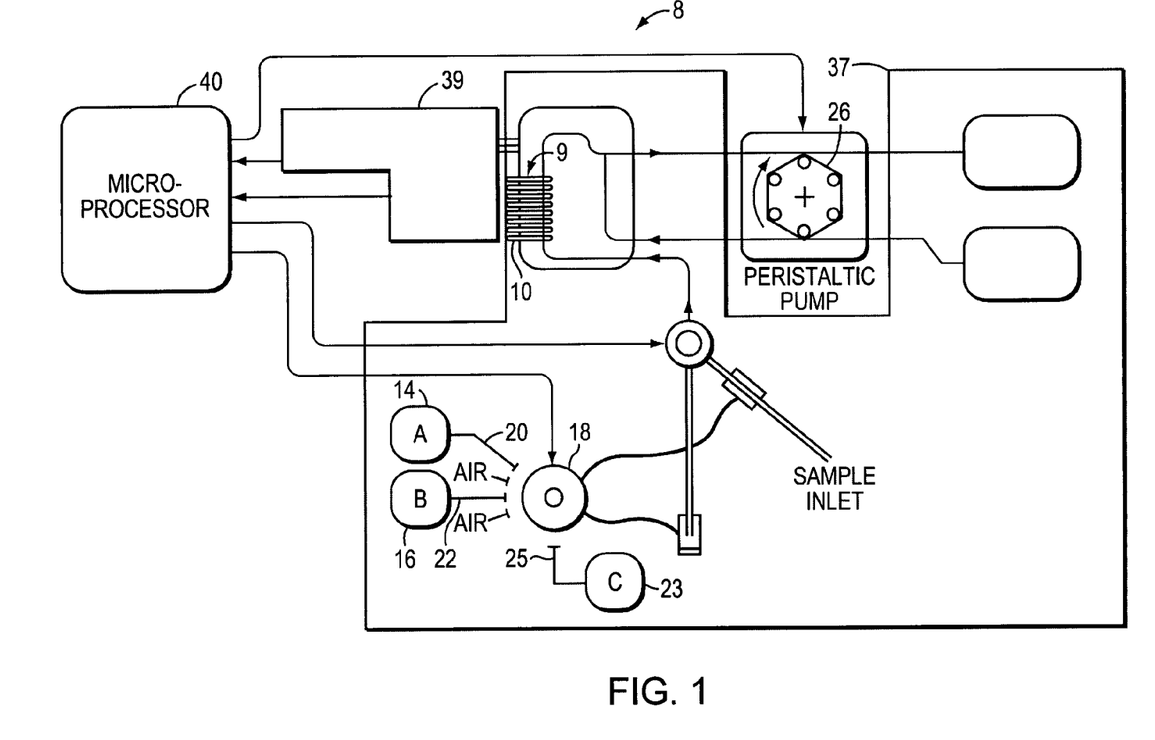
FIG. 1 is a schematic diagram of the components of an electrochemical sensor apparatus including a sensor cartridge with a bank of sensors and a thermal block for accelerated hydration and calibration of the sensors.

Referring to FIG. 1, the exemplary electrochemical sensor system 8 employs a sensor assembly, generally indicated at 10, incorporating a plurality of electrodes 9 adapted to make electrical measurements on a sample, such as a blood sample, introduced to the sensor assembly 10. Blood samples may be obtained by, for example, phlebotomy or are derived on a periodic basis from an extracorporeal blood flow circuit connected to a patient during, for example, open heart surgery. An electrochemical system of a similar type is described in U.S. Ser. No. 09/872,240, U.S. Ser. No. 09/871,885, and U.S. Ser. No. 09/872,247, the entirety of each of the three applications being incorporated by reference herein. An electrochemical system of a similar type is the GEM Premier 3000 system manufactured by Instrumentation Laboratory, Lexington, Mass. 02421.

The electrochemical sensor system 8 includes a disposable cartridge 37. A cartridge of a similar type is set forth in detail in U.S. Pat. No. 4,734,184, the entirety of which is incorporated by reference herein. Electrochemical system 8 also includes a pump 26 for drawing fluids to the electrodes 9, a heater block assembly 39 of a suitably adapted blood chemistry analysis machine, and a microprocessor 40.

In one embodiment of the invention, the electrochemical sensor system 8 incorporates in the cartridge 37 at least two prepackaged containers 14 and 16, each containing a calibration solution having known values of the parameters to be measured by electrochemical sensor system 8. For purposes of reference, the solution contained within the prepackaged container 14 will be termed calibration solution A, and the solution contained within the prepackaged container 16 will be termed calibration solution B. In another embodiment of the invention, the electrochemical sensor system 8 may include a third prepackaged container 23 containing calibration solution C. Each of the prepackaged containers 14, 16, and 23 contains a sufficient quantity of its respective calibration solution to allow electrochemical sensor system 8 to be calibrated a substantial number of times before the prepackaged container 16 becomes empty, e.g., 1000 times with calibration solution B or 100 times with calibration solution A.

Calibration Solutions and Containers

In one embodiment of the invention, a composition of calibration solution A, prepared at 37° C. and at atmospheric pressure tonometered with 9% $CO_2$, 14% $O_2$ and 77% helium gas, is as follows: pH=6.9; partial pressure of $CO_2$ ($pCO_2$)=63 mmHg; $pO_2$=100 mmHg; $Na^+$=100 mmol/L; $K^+$=7 mmol/L; $Ca^{++}$=2.5 mmol/L; $HCO_3^-$=11.5 mmol/L;

glucose=150 milligram/deciliter (mg/dL); lactate=4 mmol/L; creatine=0.4 mmol/L; creatinine=0.3 mmol/L; a biological buffer, e.g., 3-Morpholinopropanesulfonic acid (MOPS)=100 mmol/L; a surfactant, e.g., polyoxyethylene 23 lauryl ether (Brij® 35)=50 milligram/liter (mg/L); and an inert preservative, e.g., 2-methyl-4-isothiazolin-3-one hydrochloride (MIT)=0.3 gram/liter (g/L).

In another embodiment of the invention, a composition of calibration solution B, prepared at 37° C. and at 700 mmHg absolute pressure tonometered with 27% $O_2$, 5% $CO_2$, and 68% helium gas, is as follows: pH=7.4; $pCO_2$=34 mmHg; $pO_2$=180 mmHg; $Na^+$=140 mmol/L; $K^+$=3.5 mmol/L; $Ca^{++}$=1.0 mmol/L; $HCO_3^-$=20.0 mmol/L; choline chloride=20 mmol/L; a biological buffer, e.g., MOPS=100 mmol/L; a surfactant, e.g., Brij® 35=50 mg/L; and an inert preservative, e.g., MIT=0.3 g/L.

In yet another embodiment of the invention, calibration solution C contains an aqueous solution of $Na^+$, $K^+$, $Ca^{++}$, and $HCO_3^-$ salts with concentrations of $Na^+$=140 mmol/L, $K^+$=4 mmol/L, $Ca^{++}$=0.2 mmol/L, and $HCO_3^-$=13 mmol/L; 15 mmol/L of m-phenylenediamine, 20 mmol/L of sulfite; 50 mg/L of a surfactant, e.g., Brij® 35; 0.3 g/L of an inert preservative, e.g., MIT; 50 mmol/L of a biological buffer, e.g., MOPS; pH=7.2; and $pCO_2$=30 mmHg.

The reference solution may contain $AgNO_3$=0.5 mmol/L; $KNO_3$=1 mol/L; and a surfactant, e.g., Brij® 35=150 g/L.

The compositions of the calibration solutions A and B are chosen so that for each of the characteristics measured by electrochemical sensor system 8, e.g., a concentration of $Na^+$, a pair of values are obtained that are spaced over the range of permissible values that are measured by electrochemical sensor system, providing a balanced 2-point calibration for the instrument. The composition of the calibration solution C is selected to enable low level oxygen calibration.

The calibration solutions A and B compositions are prepared by premixing all of the constituents in a certain order, starting with the biological buffer, and then adding the salts of the $Na^+$, $K^+$, $Ca^{++}$, and $HCO_3^-$ ions, e.g., sodium bicarbonate salt ($NaHCO_3$). Glucose, lactate, creatine, and creatinine may be added to calibration solution A before or after the addition of the salts. The solution is then tonometered with oxygen and $CO_2$ mixed with helium to produce the desired level of $pCO_2$ and $pO_2$-Choline, in the form of, e.g., choline chloride, is added to calibration solution B during the addition of the salts. The concentration of choline may be selected from the range of about 5 mmol/L to about 100 mmol/L. The choline concentration may be, for example, about 20 mmol/L. Choline may also be added n the form of, e.g., one or more of the following compounds: choline hydrogen citrate, choline bitartrate, choline bicarbonate, tricholine citrate, choline ascorbate, choline borate, choline gluconate, choline phosphate, choline di(choline)sulphate and dicholine mucate The choline in calibration solution B reduces the rate of loss of oxygen content in calibration solution B. The mechanism by which choline reduces the rate of loss of oxygen content in a solution may be as follows. Choline may function by preventing the oxidation of other compounds present in the solution, and by doing so prevent consumption of the oxygen in the solution in the oxidation reaction. Choline may function to block the oxidation of the compounds by, for example, interacting with the oxygen molecule, the compound to be oxidized, or both. Choline in the solution may also alter the aqueous environment of the solution making it less conducive to an oxidation reaction.

The surfactant and the inert preservative are also added to the solution during the preparation of calibration solution A or B. These two constituents may be added to calibration solution A or B at any point during the preparation of these solutions.

The calibration solution C is prepared by a slightly different procedure. The biological buffer and certain salts (salts of $Na^+$, $K^+$, and $Ca^{++}$ ions) are added to water and the solution is tonometered with helium to bring the $pO_2$ to less than 30 mmHg. Then, the remaining chemicals (sulfite, e.g., sodium sulfite; salt of $HCO_3^-$ ions, e.g., sodium bicarbonate; and m-phenylenediamine) are added to the solution and the final mixture is tonometered with mixture of $pCO_2$ and helium to produce the desired $pCO_2$ level. The surfactant and the inert preservative are also added to the solution during the preparation of calibration solution C. These two constituents may be added to calibration solution C at any point during the preparation of this solution.

The temperature and pressure at which the calibration solutions are prepared and their method of packaging may be selected such as to preclude the possibility of dissolved gases going out of solution into the container and to minimize the tendency for gases to permeate through the extremely impermeable materials of the container. The calibration solutions may be packaged with the solutions completely filling the containers, so that there is no headspace, by evacuating the containers prior to filling in a manner which will be subsequently described. Elimination of a headspace in the container is important to prevent oxygen dissolved in the calibration solution from diffusing out of solution into the headspace. Diffusion of oxygen from the solution into the headspace may cause the rate of loss of oxygen concentration in the solution to increase in an unpredictable manner.

By filling the calibration solution into the evacuated and flexible walled prepackaged containers 14, 16, 23 at elevated temperatures and subatmospheric pressure, the solution will not have a tendency at a lower use temperature to outgas and thus produce gas bubbles in the container. Were outgassing to occur, the concentrations of the gases in the solution would be affected, possibly creating an unpredictable oxygen concentration in the solution. Similarly, the calibration solutions are preferably not packaged at a pressure that is too low, i.e., not below about 625 mm of mercury, because the absorptive capacity of the solution for gases may increase as the packaging pressure decreases, and below that pressure value the absorptive capacity of the solution may be sufficiently high to draw gases in through the slight inherent permeability of even the most gas impervious flexible packaging material, over long periods of time. Accordingly, a packaging pressure in the range of 625-700 mm of mercury is preferred.

In one embodiment, the calibration solution may be prepared at a temperature in excess of its intended use temperature, thereby reducing the tendency for outgassing of the dissolved gases at the lower temperature. This cooperates with the reduced pressure packaging to minimize the possibility of outgassing. Calibration solutions A and B may each be, for example, prepared at a temperature above their respective intended use temperature at a controlled pressure close to atmospheric pressure. Through use of elevated temperature (e.g., 37° C.), the calibration solutions may be prepared at about atmospheric pressure without any possibility of subsequent microbubbles within the container or gas transfer through the container when packaged in a zero headspace flexible gas impervious container.

The calibration solution prepackaged containers 14, 16, 23 may be formed from envelopes. These envelopes may be formed, for example, of rectangular sheets, heat sealed at the edges and heatsealed at one corner to an inlet stem of the valve 18 that is used for filling purposes. In the illustrated preferred embodiment, the prepackaged containers 14, 16, and 23 and the prepackaged container lines 20, 22, and 25 are formed in a unitary cluster with the valve 18 so that gas phase dead space in the lines 20, 22, 25 is thereby avoided. In a preferred procedure for purging and filling the envelope bags, a bag is first evacuated and then filled with the prepared solution. The bag is then shaken while the excess solution continually flows out of the bag. This process removes any residual gas bubbles from the bag. The solution is then sealed in the container. In a preferred embodiment, prepackaged containers 14, 16, and 23 include gas-impermeable containers that substantially prevent oxygen from diffusing into or out of the container, either of which would alter the estimated oxygen content used for calibrating the oxygen sensor.

The calibration solutions in the prepackaged containers 14, 16, and 23 have excellent stability and a long shelf life. When the calibration solutions A, B, and C are at use temperature and atmospheric pressure, there is minimal possibility of any outgassing from the liquid to form gas bubbles within the prepackaged containers 14, 16, and 23. To further improve the shelf life of the calibration solution B and all embodiments of the invention that include calibration solution B, the fluctuation in oxygen content in the calibration solution B may be stabilized. Choline chloride may be added to calibration solution B to reduce the rate of loss of oxygen content of the solution, thus stabilizing the oxygen content in the solution.

Oxygen Sensor Calibration

The oxygen sensor of the electrochemical sensor system may be calibrated at an upper calibration point with reference to the calibration solution B and at a lower calibration point with reference to the calibration solution C. The calibration solution C has an oxygen concentration of approximately zero as a result of the oxygen scavenger sulfite present in the solution. In one embodiment according to the invention, the calibration solution B is originally formulated to contain an original oxygen content of 180 mmHg.

The oxygen content of calibration solution B tends to decrease over time and thus differs from the original oxygen content at a time point following the starting time point of the solution. This decrease in the oxygen content may be measured by the rate of loss of oxygen content of calibration solution B. The underlying cause of the rate of loss of oxygen content of the calibration solution B may be the diffusion of oxygen out of the solution or an oxidation reaction occurring in the solution. The rate of loss of oxygen content of the solution may also vary unpredictably between different batches of an identical calibration solution due to, for example, variations in materials from which the calibration bag is made, variations in the process of sealing the calibration bag, variations in storage temperature during the shelf life, and impurities that may be present in the calibration solution B.

An unpredictable rate of loss of oxygen content in the calibration solution B may cause the estimated oxygen content to differ from the oxygen content of calibration solution B. This difference in values between the estimated oxygen content and the actual oxygen content of calibration solution B may result in the miscalibration of the oxygen sensor. Calibration of an oxygen sensor occurs by assigning the value of the estimated oxygen content of calibration solution B to the measurement by the oxygen sensor of the oxygen content of calibration solution B. The degree to which the estimated oxygen content of calibration solution B differs from the oxygen content of calibration solution B is the degree of error of the calibration of the oxygen sensor.

Choline, when added to a solution containing oxygen, decreases the rate of loss of oxygen content from a solution, and thus stabilizes the oxygen content in the solution. A stabilized rate of loss of oxygen content reduces the potential degree of difference between the estimated oxygen content and oxygen content in the calibration solution B, thus allowing for an increased accuracy in the calibration of the oxygen sensor. The increased accuracy of the calibration of the oxygen sensor also extends the useful life span of the calibration solution B. The extended useful life span of calibration solution B is due to the increased amount of time that must elapse for a difference between the estimated oxygen content and oxygen content of calibration solution B to become sufficiently large to prevent an accurate calibration of the oxygen sensor.

EXEMPLIFICATION

Test samples of different calibration solutions labeled sample 1, sample 2, sample 3, sample 4, and sample 5, were prepared as follows. Samples 1 and 2 were identical to calibration solution B without added choline chloride. Samples 1 and 2 contained 15 and 30 units/ml of heparin, respectively. Heparin is a compound known to increase oxygen decay rates, and added to samples 1-5 functions to simulate an oxygen degrading compound that may be found in calibration solution B. Samples 3, 4, and 5 were identical to calibration solution B with 20 mmol/L of added choline chloride. Sample 3 and 4 included 30 units/ml of heparin and were otherwise identical in their composition. Sample 5 differed from samples 3 and 4 by including 60 units/ml of heparin. Thus, samples 2, 3, and 4 had identical concentrations of heparin, samples 3 and 4 included choline chloride, and sample 2 did not include choline chloride.

Figure 2:
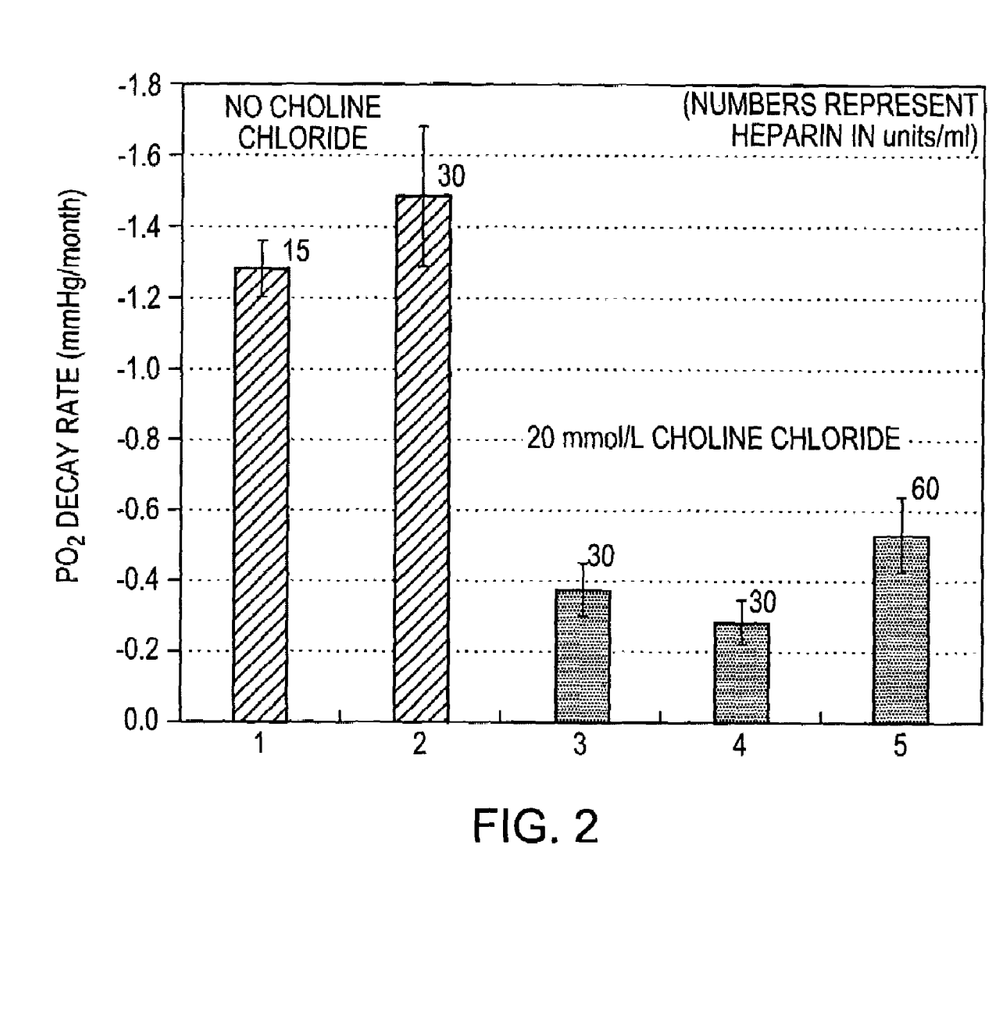
FIG. 2 depicts a bar graph of rates of loss of oxygen concentration of solutions in the presence or absence of choline chloride.

For the test, the oxygen concentrations of the five sample types were analyzed once a month for a period of 6 months. Referring to FIG. 2, a bar graph including the rate of loss of oxygen content of the five test samples is depicted. Each of the five bars depicted in FIG. 2 represents the average of three identical independently prepared samples. A significant reduction in rates of loss of oxygen content is present in samples that included choline chloride. The choline chloride in calibration solution B as part of an electrochemical sensor system solution functions similarly in lowering oxygen decay rates and thus increases the effective life span of the calibration solution B.

Choline added to calibration solution B at a concentration of 20 mmol/L or greater is sufficient to reduce the rate of loss of oxygen content in calibration solution B sufficiently to extend the effective life span of calibration solution B. Concentrations of choline less than 20 mmol/L may not reduce the rate of loss of oxygen content in calibration solution B to the same extent as a concentration of 20 mmol/L. A concentration of choline of 100 mmol/L or lower is sufficient to minimize the potential interference of choline with analytes in calibration solution B, or with electrodes in which calibration solution B makes contact. The addition of choline to calibration solution B in concentrations greater than 100 mmol/L increases the potential that interference may occur between choline in calibration solution B and analytes in calibration solution B, or between choline in calibration solution B and electrodes which contact calibration solution B.

The function of choline in calibration solution B is readily applied to other oxygen-containing solutions. An aspect of the invention relates to a method of stabilizing the oxygen content of a solution by the addition of choline to the solution. This method is applicable to any type of solution that contains dissolved oxygen and it is beneficial for the oxygen content of the solution to remain stable. This includes solutions related to clinical, pharmaceutical, and industrial applications.

The invention may be embodied in other specific forms without departing from the spirit or essential characteristics thereof. The foregoing embodiments are therefore to be considered in all respects illustrative rather than limiting of the invention described herein. The scope of the invention is thus indicated by the appended claims rather than by the foregoing description, and all changes which come within the meaning and range of equivalency of the claims are therefore intended to be embraced herein.

What is claimed is:

1. A solution for the calibration of an oxygen sensor, the solution comprising:
   a selected concentration of choline;
   $HCO_3^-$; and
   a known oxygen content,
   wherein said selected concentration of choline is sufficient to reduce a rate of loss of oxygen content in said solution, and said known oxygen content in said solution is sufficient for calibration of the oxygen sensor.

2. The solution of claim 1 wherein said rate of loss of oxygen content in said solution is in the range of about 0.05 mmHg/month to about 5.0 mmHg/month.

3. The solution of claim 1, wherein choline comprises choline chloride.

4. The solution of claim 1, wherein choline comprises a compound selected from the group consisting of choline hydrogen citrate, choline bitartrate, choline bicarbonate, tricholine citrate, choline ascorbate, choline borate, choline gluconate, choline phosphate, choline di(choline)sulphate and dicholine mucate.

5. The solution of claim 1, wherein the concentration of said choline is in a range of about 5 mmol/L to about 100 mmol/L.

6. The solution of claim 1, wherein the concentration of said choline comprises about 20 mmol/L.

7. The solution of claim 1, wherein said oxygen content is selected from a range of about 10 mmHg to 300 mmHg.

8. The solution of claim 7, wherein said oxygen content comprises about 100 mmHg.

9. The solution of claim 7, wherein said oxygen content comprises about 180 mmHg.

10. The solution of claim 1, further comprising $CO_2$.

11. The solution of claim 1, further comprising helium gas.

12. The solution of claim 1, further comprising $Na^+$.

13. The solution of claim 1, further comprising $K^+$.

14. The solution of claim 1, further comprising $Ca^{++}$.

15. The solution of claim 1, further comprising a surfactant.

16. The solution of claim 1, further comprising an inert preservative.

17. The solution of claim 1, further comprising a biological buffer.

18. A container of calibration solution for calibrating an electrochemical sensor, the container of calibration solution comprising:
    the calibration solution, comprising:
      a selected concentration of choline;
      $HCO_3^-$; and,
      a known oxygen content, wherein said selected concentration of choline is sufficient to reduce a rate of loss of oxygen content in said solution, and said known oxygen content in the solution is sufficient for calibration of an oxygen sensor; and
    a substantially gas-impermeable wall for holding the calibration solution.

19. The container of calibration solution of claim 18, wherein said container comprises at least one flexible wall.

20. The container of calibration solution according to claim 18, wherein said container is sealed to prevent a headspace comprising a gas.

21. The container of calibration solution according to claim 18, wherein said choline comprises choline chloride.

22. The container according to claim 18, wherein said choline comprises a compound selected from the group consisting of choline hydrogen citrate, choline bitartrate, choline bicarbonate, tricholine citrate, choline ascorbate, choline borate, choline gluconate, choline phosphate, choline di(choline)sulphate, and dicholine mucate.

23. The container according to claim 18, wherein said known concentration of choline is selected from the range of about 5 mmol/L to about 100 mmol/L.

24. The container according to claim 23, wherein said known concentration of choline comprises about 20 mmol/L.

25. The container according to claim 18, wherein said known oxygen content is selected from the range of about 10 mmHg to 300 mmHg.

26. The container according to claim 25, wherein said oxygen content comprises about 100 mmHg.

27. The container according to claim 26, wherein said oxygen content comprises about 180 mmHg.

28. The container according to claim 18, wherein said solution comprises $CO_2$.

29. The container according to claim 18, wherein said solution comprises helium gas.

30. The container according to claim 18, wherein said solution comprises $Na^+$.

31. The container according to claim 18, wherein said solution comprises $K^+$.

32. The container according to claim 18, wherein said solution comprises $Ca^{++}$.

33. The container according to claim 18, wherein said solution comprises a surfactant.

34. The container according to claim 18, wherein said solution comprises an inert preservative.

35. The container according to claim 18, wherein said solution comprises a biological buffer.

36. A method of reducing a rate of loss of oxygen content in a solution, comprising:
    providing the solution having a known oxygen content and comprising $HCO_3^-$; and
    adding an amount of choline to the solution,
    wherein said choline amount is sufficient to reduce said rate of loss of oxygen content in the solution.

37. The method of claim 36, wherein the amount of choline added to said solution is selected from a range of about 5 mmol/L to 100 mmol/L.

38. The method of claim 37, wherein the amount of choline added to the solution comprises about 20 mmol/L.

39. The method of claim 36, wherein choline comprises choline chloride.

40. The method of claim 36, wherein said oxygen content is in a range of about 10 mmHg to about 300 mmHg.

41. The method of claim 40, wherein said oxygen content comprises about 100 mmHg.

42. The method of claim 40, wherein said oxygen content comprises about 180 mmHg.

43. The method of claim 36, wherein said solution comprises a calibration solution.

44. The method of claim 36, wherein choline comprises a compound selected from the group consisting of choline hydrogen citrate, choline bitartrate, choline bicarbonate, tricholine citrate, choline ascorbate, choline borate, choline gluconate, choline phosphate, choline di(choline)sulphate and dicholine mucate.

45. The method of claim 36, wherein said solution comprises $CO_2$.

46. The method of claim 36, wherein said solution comprises helium gas.

47. The method of claim 36, wherein said solution comprises $Na^+$.

48. The method of claim 36, wherein said solution comprises $K^+$.

49. The method of claim 36, wherein said solution comprises $Ca^{++}$.

50. The method of claim 36, wherein said solution comprises a surfactant.

51. The method of claim 36, wherein said solution comprises an inert preservative.

52. The method of claim 36, wherein said solution comprises a biological buffer.

* * * * *